United States Patent
Su et al.

(10) Patent No.: US 11,967,182 B2
(45) Date of Patent: Apr. 23, 2024

(54) INTELLIGENT ANALYSIS SYSTEM APPLIED TO ETHOLOGY OF VARIOUS KINDS OF HIGH-DENSITY MINIMAL POLYPIDES

(71) Applicant: SHIHEZI UNIVERSITY, Shihezi (CN)

(72) Inventors: Jie Su, Shihezi (CN); Chen Fang, Shihezi (CN); Jianping Zhang, Shihezi (CN); Jiamin Gu, Shihezi (CN)

(73) Assignee: SHIHEZI UNIVERSITY, Shihezi (CN)

(*) Notice: Subject to any disclaimer, the term of this patent is extended or adjusted under 35 U.S.C. 154(b) by 0 days.

(21) Appl. No.: 18/449,412

(22) Filed: Aug. 14, 2023

(65) Prior Publication Data
US 2023/0401896 A1 Dec. 14, 2023

Related U.S. Application Data

(63) Continuation of application No. PCT/CN2023/074712, filed on Feb. 7, 2023.

(30) Foreign Application Priority Data

Mar. 3, 2022 (CN) .......................... 202210201354.7

(51) Int. Cl.
*G06V 40/20* (2022.01)
*G06T 7/80* (2017.01)
(Continued)

(52) U.S. Cl.
CPC ................ *G06V 40/20* (2022.01); *G06T 7/80* (2017.01); *G06V 20/41* (2022.01); *G06V 20/693* (2022.01);
(Continued)

(58) Field of Classification Search
CPC ...... G06V 40/20; G06V 20/41; G06V 20/693; G06V 20/698; G06T 7/80; G06T 2207/10016; G06T 2207/30188; A01K 29/005
See application file for complete search history.

(56) References Cited

U.S. PATENT DOCUMENTS

2018/0075336 A1* 3/2018 Huang .................... G06N 3/045
2022/0159934 A1* 5/2022 Molloy ................ A01K 29/005
(Continued)

FOREIGN PATENT DOCUMENTS

AU       2020103130 A4    1/2021
AU       2021100234 A4    4/2021
(Continued)

OTHER PUBLICATIONS

First Office Action for China Application No. 202210201354.7, dated Sep. 7, 2022.
(Continued)

*Primary Examiner* — Ming Y Hon
(74) *Attorney, Agent, or Firm* — Pilloff Passino & Cosenza LLP; Sean A. Passino; Rachel K. Pilloff

(57) ABSTRACT

An intelligent analysis system applied to ethology of various kinds of high-density minimal polypides is provided, including an operating platform subsystem and an analysis subsystem; the operating platform subsystem is used for providing an activity medium capable of obtaining behaviors of the minimal polypides and shooting the behaviors of the minimal polypides; the behavior collecting module in the analysis subsystem is used for obtaining an ethology video of the high-density minimal polypides through the operating platform subsystem; the analysis modeling module is used for obtaining ethology big data of various kinds of high-density minimal insects according to the ethology video, and establishing an ethology model; the simulation predicting module is used for dynamically predicting comprehensive
(Continued)

control strategies and control effects of minimal pests in a field ecosystem according to the ethology model; the visual demonstrating module is used for displaying the above behavior data.

5 Claims, 6 Drawing Sheets

(51) Int. Cl.
  *G06V 20/40* (2022.01)
  *G06V 20/69* (2022.01)
  *A01K 29/00* (2006.01)
(52) U.S. Cl.
  CPC .......... *G06V 20/698* (2022.01); *A01K 29/005* (2013.01); *G06T 2207/10016* (2013.01); *G06T 2207/30188* (2013.01)

(56) References Cited

U.S. PATENT DOCUMENTS

| | | | | |
|---|---|---|---|---|
| 2022/0383652 | A1* | 12/2022 | Seybold | A01K 29/005 |
| 2022/0392017 | A1* | 12/2022 | Datta | G06T 3/4046 |
| 2023/0070719 | A1* | 3/2023 | Jeon | G06V 40/10 |
| 2023/0084267 | A1* | 3/2023 | Tsujimoto | G16H 70/60 705/2 |

FOREIGN PATENT DOCUMENTS

| | | |
|---|---|---|
| CN | 102722716 A | 10/2012 |
| CN | 105987685 A | 10/2016 |
| CN | 108522342 A | 9/2018 |
| CN | 110276278 A | 9/2019 |
| CN | 111144236 A | 5/2020 |
| CN | 111667480 A | 9/2020 |
| CN | 112167201 A | 1/2021 |
| CN | 112580552 A | 3/2021 |
| CN | 113298023 A | 8/2021 |
| CN | 113963298 A | 1/2022 |
| CN | 114549516 A | 5/2022 |

OTHER PUBLICATIONS

Notice of Grant for China Application No. 202210201354.7, dated Dec. 7, 2022.
First Search Report for China Application No. 202210201354.7.
International Report for PCT.CN2023/074712, dated May 24, 2023.

* cited by examiner

INTELLIGENT ANALYSIS SYSTEM APPLIED TO ETHOLOGY OF VARIOUS KINDS OF HIGH-DENSITY MINIMAL POLYPIDES

CROSS-REFERENCE TO RELATED APPLICATIONS

This application is a continuation of PCT/CN 2023/074712, filed on Feb. 7, 2023, and claims priority of Chinese Patent Application No. 202210201354.7, filed on Mar. 3, 2022, the entire contents of which are incorporated herein by reference.

TECHNICAL FIELD

The disclosure belongs to the technical field of biological behavior research, and in particular to an intelligent analysis system applied to ethology of various kinds of high-density minimal polypides.

BACKGROUND

Since the rapid development of the deep learning technology, it has become an inevitable trend to use computers to visually process and analyze the video data from all walks of life, so as to improve the detection accuracy and efficiency of targets and reduce costs. In the field of plant protection (especially for minimal targets, such as mites), there is not a mature analysis system to meet the needs of quantitative analysis and modeling of various kinds of high-density ethology in the research and analysis of predation ethology between natural enemies and pests, between different natural enemies and between different pests. Most researchers may only adopt a research model based on manual observation and statistics aided by computer analysis, and this research model directly leads to low research efficiency and high error, and is limited by a single or small number of polypides. As a result, the research model has a single factor and cannot fit the biotope where many random factors coexist in the field. With the continuous development of computer technology, many researchers have strengthened the weight of computer-aided research and development design, innovated many research methods by using machine vision, and achieved remarkable results in ethology analysis of single or a few insects clearly visible to the naked eye. However, these innovations may not meet the ethology research and analysis of minimal insects in the habitat of damaged plant leaves at a high density.

SUMMARY

The disclosure provides an intelligent analysis system applied to ethology of various kinds of high-density minimal polypides, which may digitize the whole process of complex ethology and establish large data sets, and provide basic big data for calculating important ethology parameters and the exploring and excavating deeper, more dimensional and higher-density systematic complex biological problems.

In order to achieve the above objective, the disclosure provides the following scheme.

An intelligent analysis system applied to ethology of various kinds of high-density minimal polypides includes an operating platform subsystem and an analysis subsystem;

the operating platform subsystem is used for providing an activity medium capable of obtaining behaviors of the minimal polypides and shooting the behaviors of the minimal polypides;

the analysis subsystem includes a behavior collecting module, an analysis modeling module, a simulation predicting module and a visual demonstrating module;

the behavior collecting module is used for obtaining an ethology video of the high-density minimal polypides through the operating platform subsystem;

the analysis modeling module is used for obtaining ethology big data of various kinds of high-density minimal insects according to the ethology video, and establishing an ethology model based on the ethology big data;

the simulation predicting module is used for dynamically predicting comprehensive control strategies and control effects of minimal pests in a field ecosystem according to the ethology model; and the visual demonstrating module is used for displaying the ethology video, the ethology model and the comprehensive control strategies and effects.

Optionally, the operating platform subsystem includes an activity medium and a video collecting device;

The activity medium is a tissue structure of injured plants, and a range of the activity medium is designed by using a silk moisturizing material on a surface structure of the tissue structure; and the video collecting device is used for shooting high-density minimal polypide insects.

Optionally, the operating platform subsystem further includes an isolation box and a universal movable device;

the activity medium and the video collecting device are located in the isolation box, and the isolation box is used for avoiding negative influence factors, and the negative influence factors are interference factors suffered by the video collecting device in a shooting process; and the video collecting device is connected with the universal movable device, and the universal movable device is used for adjusting a spatial position of the video collecting device.

Optionally, the behavior collecting module includes an image calibration unit and a shooting control unit;

the image calibration unit is used for generating shooting adjustment data according to images shot by the video collecting device; and the shooting control unit is used for adjusting the spatial position and shooting parameters of the video collecting device according to the shooting adjustment data.

Optionally, the analysis modeling module includes a biological individual identification unit, a biological individual behavior unit and a modeling unit;

the biological individual identification unit is used for identifying biological individuals in the ethology video according to biological characteristics;

the biological individual behavior unit is used for analyzing behavioral actions of the biological individuals and obtaining the ethology big data of the biological individuals; and the modeling unit is used for establishing the ethology model according to the ethology big data.

Optionally, the modeling unit includes an ethology linear model and an ethology nonlinear model;

the ethology linear model includes an average rate, an instantaneous rate, a step length, the movement trajectory, an attack power, a predation duration, a predation success rate of the biological individual; and Based on the ethology linear model, the ethology nonlinear model is established.

Optionally, the biological individual behavior unit includes a positioning subunit and a tracking subunit;

the positioning subunit is used for positioning position information of a whole process of a biological individual behavior; and the individual tracking subunit is used for recording the position information of the whole process of the biological individual behavior.

Optionally, the positioning subunit of an individual and the tracking subunit of the individual both adopt a minimal polypide monitoring algorithm.

Optionally, the simulation predicting module includes a simulation unit and a comprehensive predicting unit;

the simulation unit is used for simulating minimal pests' occurrence data in the field ecosystem; and the comprehensive predicting unit is used to obtain the comprehensive control strategies and expected control effects according to the ethology model of the minimal pests.

The embodiment has the following beneficial effects.

The embodiment discloses an intelligent analysis system applied to ethology of various kinds of high-density minimal polypides, which may accurately and efficiently obtain the big data resources of the minimal pests ethology in the field as the production end, and carry out multi-dimensional analysis and modeling, thus providing a favorable tool for researchers to explore the behavior mechanism among biological communities in the field ecosystem, and give the essence of IPM (integrated pest management) into full play.

BRIEF DESCRIPTION OF THE DRAWING

In order to explain the technical scheme of this disclosure more clearly, the FIGURE needed in the embodiments is briefly introduced below. Obviously, the FIGURE in the following description is only for some embodiments of this disclosure. For ordinary technicians in this field, other FIGURES may be obtained according to the FIGURE without paying creative labor.

DETAILED DESCRIPTION OF THE EMBODIMENTS

Figure 1:
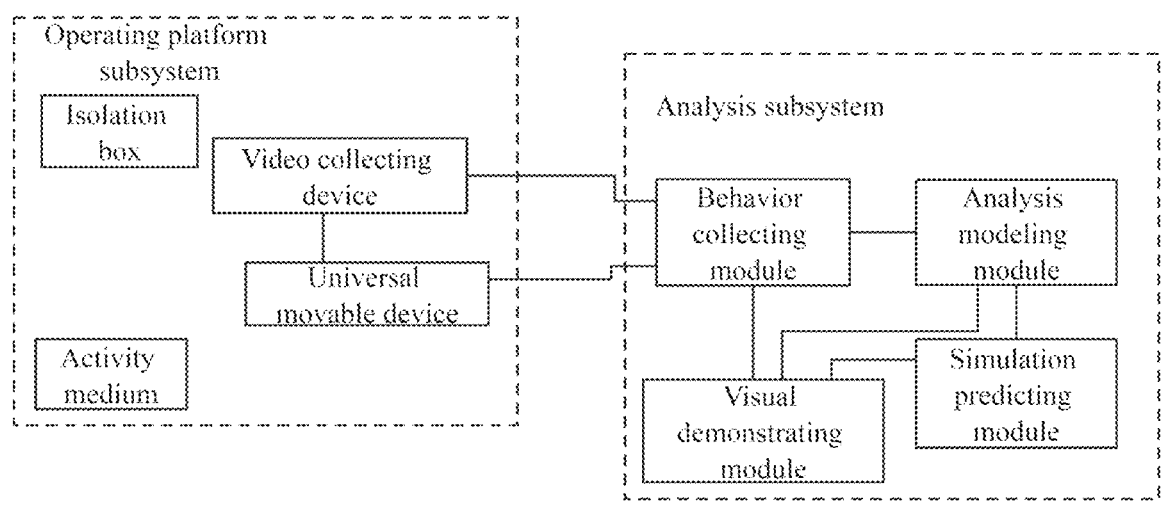
FIG. 1 is a schematic structural diagram of an intelligent analysis system applied to ethology of various kinds of high-density minimal polypides according to the embodiment of the present disclosure.
Figure 2:
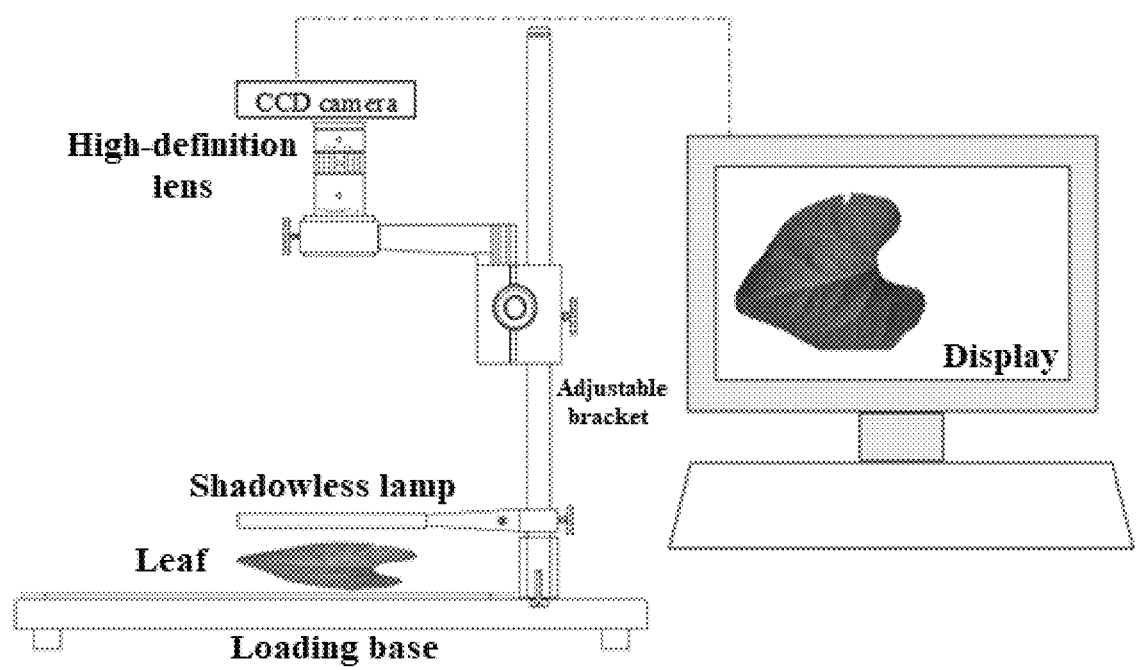
FIG. 2 showing a schematic structural diagram of a video collecting device.
Figure 3:
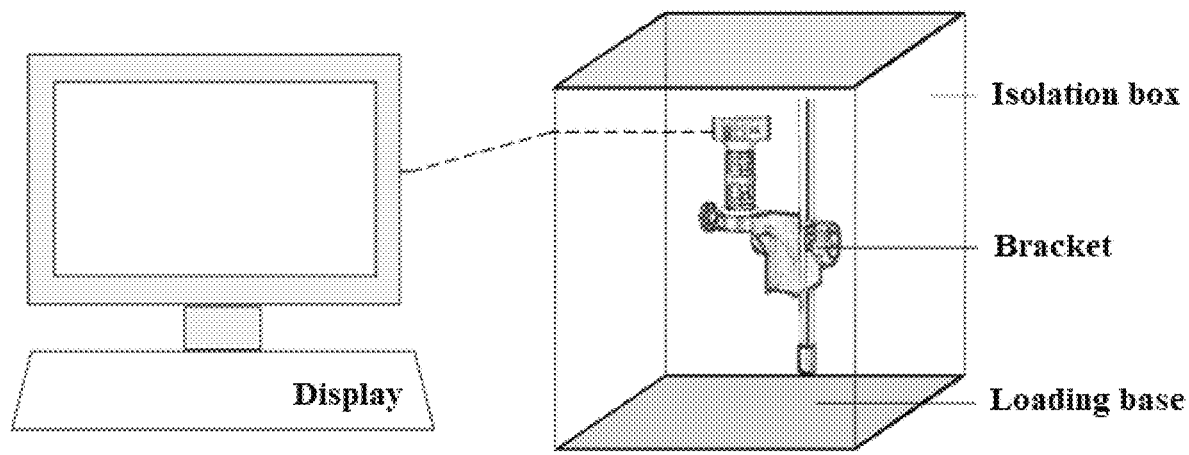
FIG. 3 showing a behavior collecting module consists of a display, an isolation box, a CCD camera connected with a high-definition wide-angle lens, a loading base and an adjustable bracket.
Figure 4:
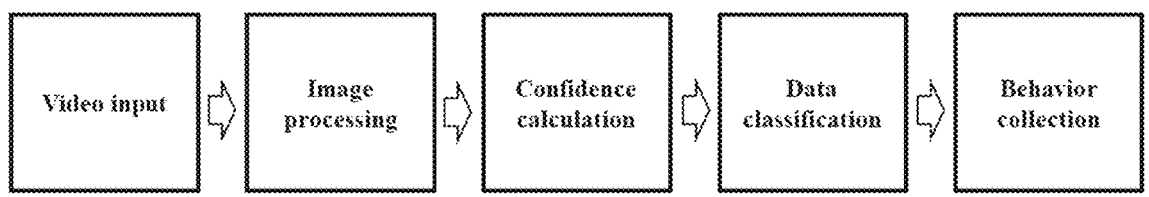
FIG. 4 showing the schematic structural diagram of biological individual identification method.
Figure 5:
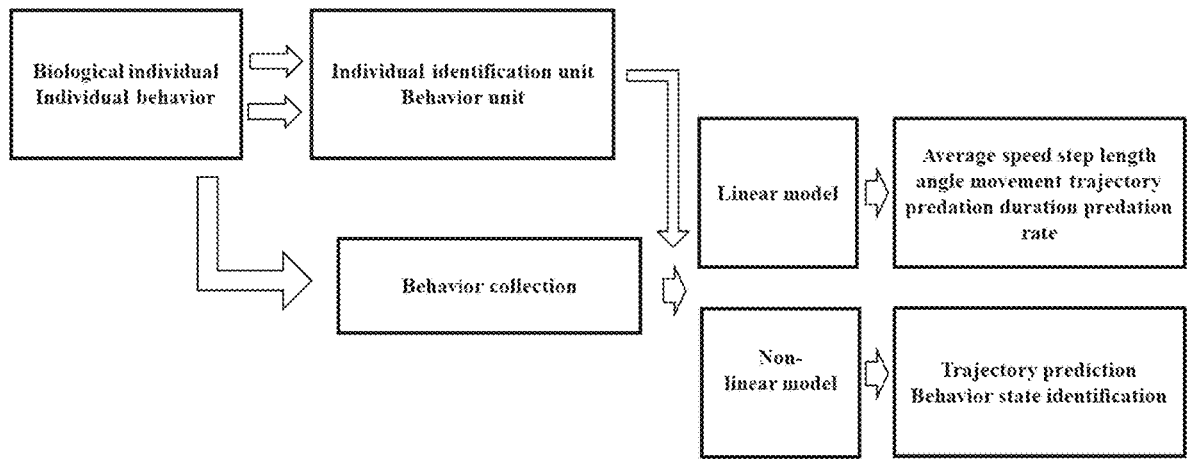
FIG. 5 showing the schematic structural diagram of analysis modeling module.
Figure 6:
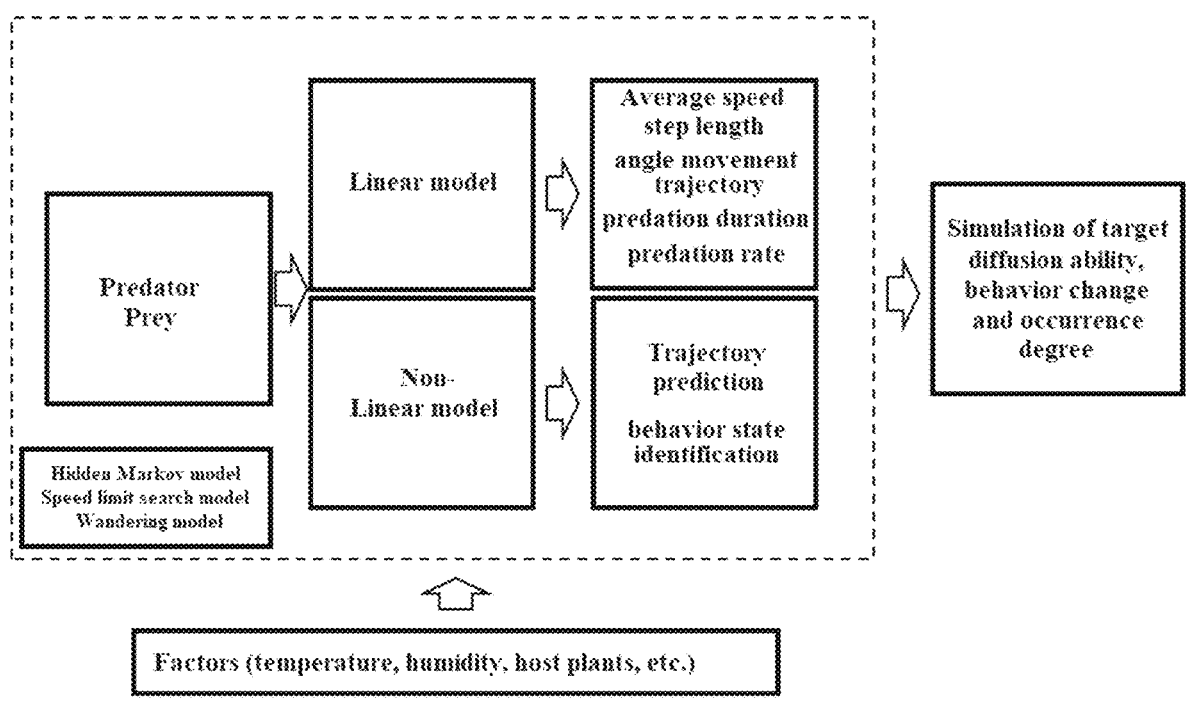
FIG. 6 showing the schematic structural diagram of simulation predicting module.
Figure 7:
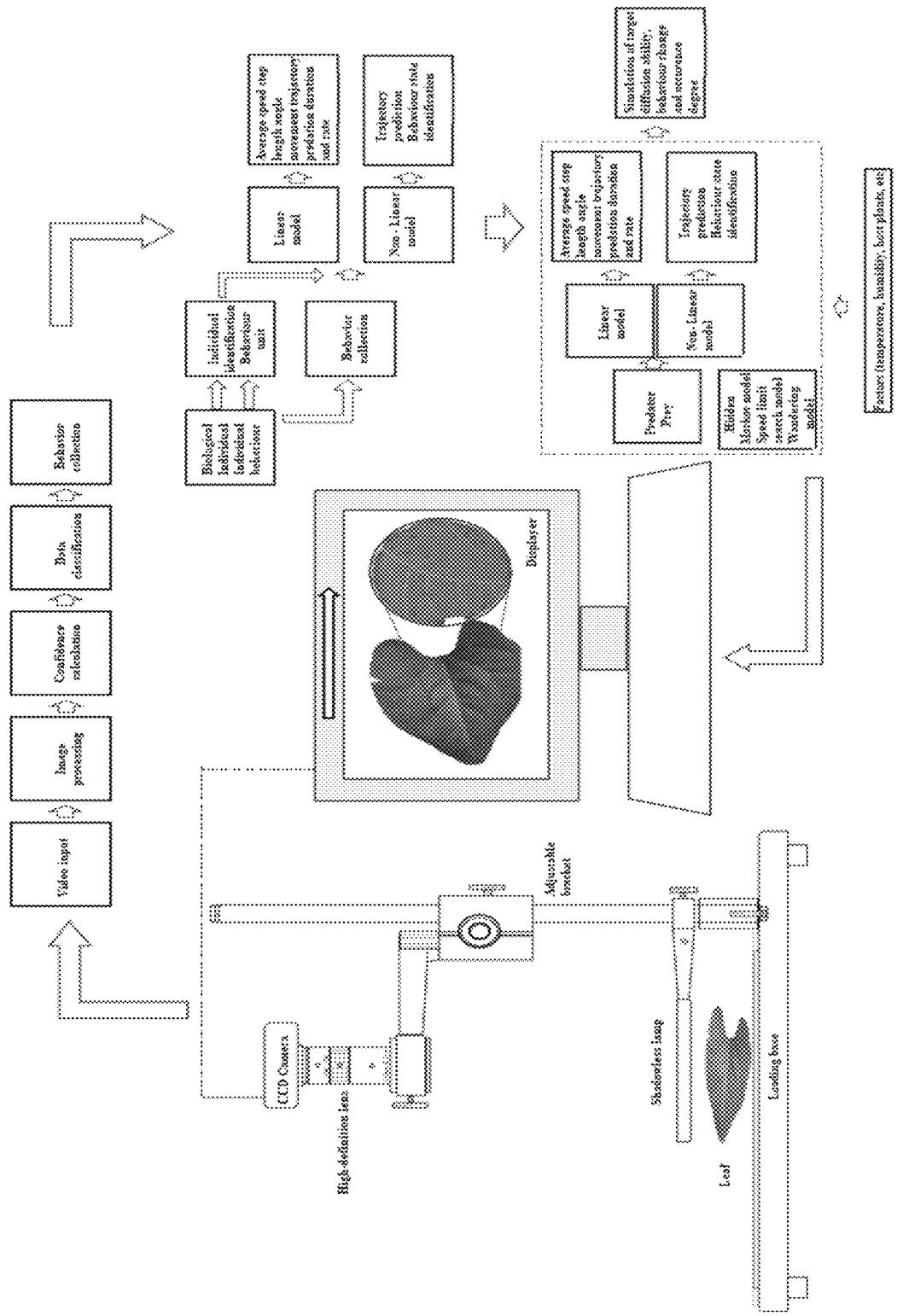
FIG. 7 showing the schematic structural diagram of visual demonstrating module.

In the following, the technical scheme in the embodiment of the disclosure will be clearly and completely described with reference to the FIGURES in the embodiment of the disclosure. Obviously, the described embodiment is only a part of the embodiment of the disclosure, but not the whole embodiment. Based on the embodiment in this disclosure, all other embodiments obtained by ordinary technicians in this field without creative work belong to the protection scope of this disclosure.

In order to make the above objectives, features and advantages of this disclosure more obvious and easier to understand, the disclosure will be further described in detail with the FIGURE and specific embodiment.

The FIGURE is a schematic structural diagram of an intelligent analysis system applied to ethology of various kinds of high-density minimal polypides, which mainly includes two parts: an operating platform subsystem and an analysis subsystem.

Specifically, the operating platform subsystem is used for providing an activity medium capable of obtaining behaviors of the minimal polypides and shooting the behaviors of the minimal polypides.

The analysis subsystem includes a behavior collecting module, an analysis modeling module, a simulation predicting module and a visual demonstrating module. The behavior collecting module is used for obtaining an ethology video of the high-density minimal polypides through the operating platform subsystem. The analysis modeling module is used for obtaining ethology big data of various kinds of high-density minimal insects according to the ethology video, and establishing an ethology model based on the ethology big data. The simulation predicting module is used for dynamically predicting comprehensive control strategies and control effects of minimal pests in a field ecosystem according to the ethology model. The visual demonstrating module is used for displaying the ethology video, the ethology model and the comprehensive control strategies and effects.

Next the structural composition and functional realization of the above components in this embodiment will be described in detail.

In this embodiment, the operating platform subsystem mainly includes an activity medium and a video collecting device. The activity medium is the tissue structure of the inflicted plant, that is, fresh leaves. Besides, the range of the activity medium is designed by fully considering the influence of leaf surface structure and combining with the water dungeon, so as to fully simulate the relationship between the actual activities of minimal polypide pests and the influence of plant leaf surface structure, and greatly enhance the fitting degree of experimental design and field habitat.

The video collecting device is composed of a microscope and a high-definition lens, which are integrated into one design. The high-definition lens is connected with the eyepiece of the microscope, and meanwhile, the quasi-focus adjustment of the microscope and the shooting parameters of the high-definition lens may be adjusted separately. The high-density minimal polypide insects are found through the microscope, and then the shooting is completed through the high-definition lens. In this embodiment, taking mites as the target organism, the biological behavior research is carried out.

Further, in order to avoid the interference of negative factors such as noise, illumination, etc. that the high-definition lens may be subjected to in the shooting process, in this embodiment, an isolation box is added to put the activity medium and the high-definition lens in the isolation box, which provides an ideal environment for the natural activities of mites and high-definition shooting.

Furthermore, in this embodiment, a universal movable device is added to adjust the spatial position of the video collecting device to meet the fine-tuning linkage of the video collecting device, including the distance, orientation and shooting angle of the video collecting device from the activity medium.

Based on the operating platform subsystem designed in this embodiment, the corresponding analysis subsystem designed in this embodiment is composed of behavior collecting module, analysis modeling module, simulation predicting module and visual demonstrating module.

In this embodiment, the behavior collecting module consists of an image calibration unit and a shooting control unit. The image calibration unit is linked with the shooting control unit, and the shooting control unit respectively adjusts the calibration of the microscope and the parameters of the high-definition lens; image calibration unit generates shooting adjustment data according to the images shot by the high-definition lens and the changes of the image definition; the shooting control unit is used for adjusting the spatial position and shooting parameters of the video collecting device according to the shooting adjustment data; firstly the distance and spatial position relationship between the high-definition lens and the microscope eyepiece are adjusted, ensuring that the image in the eyepiece shot by the high-definition lens may be the clearest; then the distance between the objective lens of the microscope and the activity medium is adjusted to make the image in the eyepiece clear; finally the spatial position relationship between the whole video collecting device and the activity medium is adjusted to obtain the expected shooting angle and shooting content. During this adjustment process, the calibration of the microscope may be adjusted in real time to ensure that the image in the eyepiece shot by the high-definition lens is clear.

Under the control of the behavior collecting module, the video collecting device is driven to clearly shoot the individual behavior of mites, so as to obtain high-definition ethology videos.

Based on minimal biological individuals of mites, in this embodiment, the analysis modeling module consists of a biological individual identification unit, a biological individual behavior unit and a modeling unit. The biological individual identification unit is used to identify each biological individual in the ethology video according to the biological feature vector. Because the mites are small and numerous, accurately identifying each mite is the premise of later behavior research.

The biological individual behavior unit is used to analyze the behavior of each biological individual and obtain the ethology big data of each biological individual. In this embodiment, the ethology big data includes a movement rate, an average rate, an instantaneous rate, a step length, a movement trajectory, an attack power, a predation duration, a predation success rate and so on. In this embodiment, the biological individual behavior unit is further divided into a positioning subunit and a tracking subunit. The positioning subunit is used to locate the position information of the whole process of each biological individual's behavior; the individual tracking subunit is used to record all the position information of each individual in the whole process of behavior. Both the positioning subunit and the tracking subunit study the ethology of mites through the minimal polypide monitoring algorithm to judge the current behavior of mites. In this embodiment, the minimal polypide monitoring algorithm and the pest monitoring algorithm are divided into three parts: first, the preprocessing algorithm enhances the sample data. The main process is to label the image data of many kinds of pest samples with Labelme image labeling tool, generate pseudo-color images (single channel PNG images) by channel transformation based on the labeled image, and generate target small images and background small images as training samples based on PNG images. The algorithm for generating the training samples of the target small images is to search the labeled image containing the mite target circularly, and search the mite targets in the images circularly. For each mite target, the labeled position coordinate information is obtained, and then the coordinates of the upper left corner and the lower right corner of the rectangle are randomly generated, and the Intersection-over-Union (IOU) of the randomly generated rectangle and the mite position area is calculated. If IOU is greater than 0.98, the randomly generated rectangular area is taken as the small image sample. The algorithm for generating the training sample of the background small images is to search the labeled image containing mite targets circularly, obtain the position coordinates of all the mite targets in the images, find the maximum circumscribed rectangle of these coordinates, extend four sides of the rectangle up, down, left and right respectively, divide the image into nine mutually exclusive regions, eight of which do not contain any mite targets, and randomly sample the eight regions and take screenshots to generate 1-8 background small images. Second, the recognition model is trained. Based on Bisenet (Bilateral Segmentation Network) V2, a pest identification and detection model is constructed, which realizes the high precision and high efficiency of mite semantic segmentation detection. Third, post-processing is carried out. Softmax operation is performed on the network output matrix out to obtain the confidence distribution score_map and the category distribution class_map of each pixel. Connected component analysis is performed on the class_map to obtain the position information of each target. Then, the confidence distribution of the corresponding target area on the score_map is obtained through matrix intersection. All the confidence in the area is averaged as the confidence of the target, and the target position and confidence information are output. The minimal polypide monitoring algorithm adopted in this embodiment may repeatedly avoid the contradiction of large error and low efficiency of naked eye observation method, strong randomness of digital image noise, poor technical characteristics and stability of machine learning, and high precision and long time-consuming of deep learning, and has the advantages of digital image and deep learning, and is well applicable in the field of identifying and tracking various kinds of minimal polypides, and provides assistance for studying the behavioral mechanism between pests and natural enemies.

After obtaining the ethology big data of the target organism, a new ethology model may be established through the ethology big data and make targeted biological behavior research. In this embodiment, the ethology model includes an ethology linear model and an ethology nonlinear model.

The ethology linear model includes a movement speed, a movement trajectory, an attack behavior and a predation behavior of the biological individuals. First, a behavior trajectory diagram of each biological individual is drawn to obtain ethology parameters of the biological individuals, and the ethology parameters include a movement speed, an angle change and an instantaneous speed change; and then the ethology linear model is established, consisting of a movement rate, an average rate, an instantaneous rate, a step length, the movement trajectory, an attack power, a predation duration, a predation success rate and so on.

Then, based on the linear model of behavior, the Levy's walk model of behavior and other nonlinear models are established.

In this embodiment, the simulation predicting module includes a simulation unit and a comprehensive predicting unit.

The simulation unit is used to input the data of minimal pests in the current field ecosystem, including the species, quantity and density of pests, as well as intraspecies and interspecific relationships.

The comprehensive predicting unit is used to simulate and deduce the comprehensive control strategies and corresponding control effects of minimal pests in the field ecosystem according to the data of minimal pests and the ethology model established above.

In this embodiment, the visual demonstrating module may use general display equipment to display the ethology video and ethology model in the above-mentioned process, and display the simulated comprehensive control strategies and the corresponding control effects one-on-one.

The intelligent analysis system provided by this embodiment may accurately and efficiently obtain the big data resources of the ethology of minimal pests at the field as the production end, and carry out multi-dimensional analysis and modeling, which provides a favorable tool for researchers to explore the behavior mechanism among biological communities in the field ecosystem, so as to give the essence of IPM of minimal pests into better play.

The above-mentioned embodiment is only a description of the preferred mode of this disclosure, not a limitation on the scope of this disclosure. Without departing from the design spirit of this disclosure, various modifications and improvements made by ordinary technicians in this field to the technical scheme of this disclosure shall fall within the protection scope determined by the claims of this disclosure.

What is claimed is:

1. An intelligent analysis system applied to ethology of various kinds of high-density minimal polypides, comprising an operating platform subsystem and an analysis subsystem;
   wherein the operating platform subsystem is used for providing an activity medium capable of obtaining behaviors of the minimal polypides and shooting the behaviors of the minimal polypides;
   the analysis subsystem comprises a behavior collecting module, an analysis modeling module, a simulation predicting module and a visual demonstrating module;
   the behavior collecting module is used for obtaining an ethology video of the high-density minimal polypides through the operating platform subsystem;
   the analysis modeling module is used for obtaining ethology big data of various kinds of high-density minimal insects according to the ethology video, and establishing an ethology model based on the ethology big data;
   the simulation predicting module is used for dynamically predicting comprehensive control strategies and control effects of minimal pests in a field ecosystem according to the ethology model;
   the visual demonstrating module is used for displaying the ethology video, the ethology model and the comprehensive control strategies and effects;
   the analysis modeling module comprises a biological individual identification unit, a biological individual behavior unit and a modeling unit;
   the biological individual identification unit is used for identifying biological individuals in the ethology video according to biological characteristics;
   the biological individual behavior unit is used for analyzing behavioral actions of the biological individuals and obtaining the ethology big data of the biological individuals;
   the modeling unit is used for establishing the ethology model according to the ethology big data;
   the modeling unit comprises an ethology linear model and an ethology nonlinear model;
   the ethology linear model comprises a movement speed, a movement trajectory, an attack behavior and a predation behavior of the biological individuals; first, a behavior trajectory diagram of each biological individual is drawn to obtain ethology parameters of the biological individuals, and the ethology parameters comprise a movement speed, an angle change and an instantaneous speed change; and then the ethology linear model is established, comprising a movement rate, an average rate, an instantaneous rate, a step length, the movement trajectory, an attack power, a predation duration, a predation success rate and so on;
   the ethology nonlinear model is established based on the ethology linear model;
   the biological individual behavior unit comprises a positioning subunit and a tracking subunit;
   the positioning subunit is used for positioning position information of a whole process of a biological individual behavior;
   the individual tracking subunit is used for recording the position information of the whole process of the biological individual behavior; and
   the positioning subunit of an individual and the tracking subunit of the individual both adopt a minimal polypide monitoring algorithm.

2. The intelligent analysis system applied to ethology of various kinds of high-density minimal polypides according to claim 1, wherein
   the operating platform subsystem comprises the activity medium and a video collecting device;
   the activity medium is a tissue structure of inflicted plants, and a range of the activity medium is designed by using a silk moisturizing material on a surface structure of the tissue structure; and
   the video collecting device is used for shooting high-density minimal polypide insects.

3. The intelligent analysis system applied to ethology of various kinds of high-density minimal polypides according to claim 2, wherein
   the operating platform subsystem further comprises an isolation box and a universal movable device;
   the activity medium and the video collecting device are located in the isolation box, the isolation box is used for avoiding negative influence factors, and the negative influence factors are interference factors suffered by the video collecting device in a shooting process; and
   the video collecting device is connected with the universal movable device, and the universal movable device is used for adjusting a spatial position of the video collecting device.

4. The intelligent analysis system applied to ethology of various kinds of high-density minimal polypides according to claim 3, wherein
   the behavior collecting module comprises an image calibration unit and a shooting control unit;
   the image calibration unit is used for generating shooting adjustment data according to images shot by the video collecting device; and the shooting control unit is used for adjusting the spatial position and shooting parameters of the video collecting device according to the shooting adjustment data.

5. The intelligent analysis system applied to ethology of various kinds of high-density minimal polypides according to claim 1, wherein the simulation predicting module comprises a simulation unit and a comprehensive predicting unit;

the simulation unit is used for simulating minimal pests' occurrence data in the field ecosystem; and the comprehensive predicting unit is used to obtain the comprehensive control strategies and expected control effects according to the ethology model of the minimal pests.

\* \* \* \* \*